US008075626B2

(12) United States Patent
Dun

(10) Patent No.: US 8,075,626 B2
(45) Date of Patent: *Dec. 13, 2011

(54) ORTHOPAEDIC KNEE PROSTHESIS HAVING INCREASED AXIAL-ROTATION

(75) Inventor: Shouchen Dun, Fort Wayne, IN (US)

(73) Assignee: DePuy Products, Inc., Warsaw, IN (US)

( * ) Notice: Subject to any disclaimer, the term of this patent is extended or adjusted under 35 U.S.C. 154(b) by 265 days.

This patent is subject to a terminal disclaimer.

(21) Appl. No.: 12/165,424

(22) Filed: Jun. 30, 2008

(65) Prior Publication Data

US 2009/0326663 A1    Dec. 31, 2009

(51) Int. Cl.
*A61F 2/38* (2006.01)
(52) U.S. Cl. ............... 623/20.27; 623/20.15; 623/20.21; 623/20.32; 623/20.35
(58) Field of Classification Search .............. 623/20.14, 623/20.15, 20.21, 20.27, 20.32, 20.33, 20.35, 623/20.24, 20.26, 20.28
See application file for complete search history.

(56) References Cited

U.S. PATENT DOCUMENTS

| | | | |
|---|---|---|---|
| 4,959,071 | A | 9/1990 | Brown et al. |
| 5,147,405 | A | 9/1992 | Van Zile et al. |
| 5,192,328 | A | 3/1993 | Winters |
| 5,370,699 | A | 12/1994 | Hood et al. |
| 6,013,103 | A | 1/2000 | Kaufman |
| 6,080,195 | A | 6/2000 | Colleran et al. |
| 6,986,791 | B1 | 1/2006 | Metzger |
| 7,326,252 | B2 | 2/2008 | Otto et al. |
| 2005/0055102 | A1 | 3/2005 | Tornier et al. |
| 2006/0265078 | A1 | 11/2006 | McMinn |
| 2006/0265080 | A1 | 11/2006 | McMinn |

FOREIGN PATENT DOCUMENTS

| | | |
|---|---|---|
| EP | 0970667 | 1/2000 |
| EP | 1378216 | 1/2004 |
| EP | 1400220 | 3/2004 |
| EP | 1591082 | 11/2005 |
| WO | 2004058108 A1 | 7/2004 |

OTHER PUBLICATIONS

European Search Report for European Patent Application No. 09164194.4-1526, Dec. 9, 2009, 6 pgs.
European Search Report for European Patent Application No. 09164242.1-2310/2140838, Jan. 19, 2010, 10 pgs.
NexGen Complete Knee Solution Cruciate Retaining Knee (CR), Zimmer, 2 pages, http://www.zimmer.com/z/ctl/op/global/action/1/id/356/template/PC/prcat/P3/prod/y.
Advance Stemmed Medical Pivot, Wright Medical Technology, 3 pages, http://www.wmt.com/Downloads/ADVANCE%C2%AE%20Stemmed%20Medial%20Pivot%20broc%20MK419-701.pdf.
Scorpio NRG, The Evolution in High Performance Knee System, Stryker Orthopaedics, 16 pages, http://www.stryker.com/stellent/groups/public/documents/web_prod/023608.pdf.
Performance Knee System, BIOMET, 1 page, http://www.biometgermany.de/medhome-uk/knee/primary/performance. In Vivo Determination of Posterior Femoral Rollback for Subjects Having a NexGen Posterior Cruciate-Retaining Total Knee Arthroplasty, Bertin et al., (2002), 9 pgs.
Contact stress at the post-cam mechanism in posterior-stabilized total knee arthroplasty, Nakayama et al., (2005), 6 pgs.
Kinematic Comparison Between Mobile-Bearing and Fixed-Bearing Inserts in NexGen Legacy Posterior Stabilized Flex Total Knee Arthroplasty, Shi et al., (2008), 6 pgs.
Stress Analysis of PS Type Knee Prostheses under Deep Flexion, Todo et al., (2007), 9 pgs.
Partial European Search Report for European Patent Application No. 09164242.1-2310, Oct. 19, 2009, 5 pgs.
Stryker Howmedica Osteonics, Scorpio Flex Single Axis Knee, 2002, 3 pages.

*Primary Examiner* — David H Willse
*Assistant Examiner* — Javier Blanco
(74) *Attorney, Agent, or Firm* — Barnes & Thornburg LLP

(57) ABSTRACT

An orthopaedic prosthesis includes a tibial bearing and a femoral component configured to articulate with the tibial bearing. The tibial bearing and the femoral component are configured to promote outward axial rotation of the femoral component with respect to the tibial component during knee flexion.

13 Claims, 7 Drawing Sheets

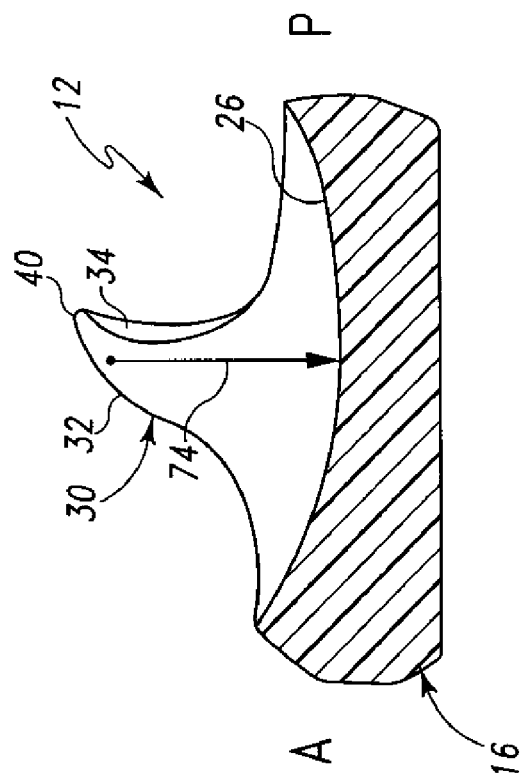
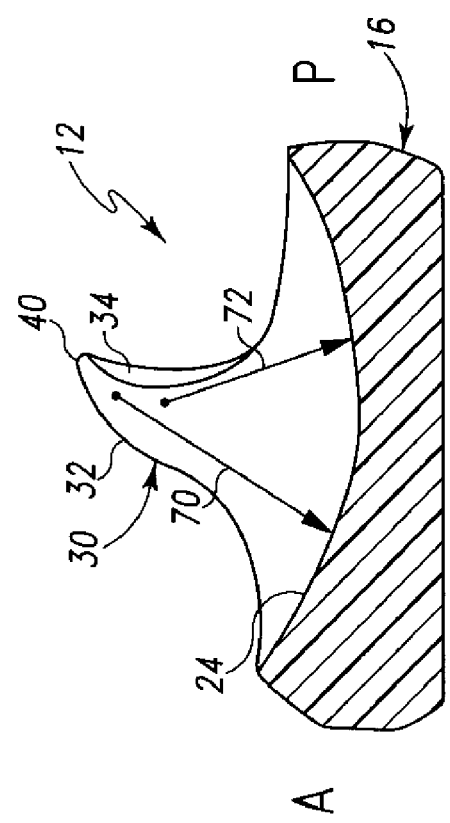

ORTHOPAEDIC KNEE PROSTHESIS HAVING INCREASED AXIAL-ROTATION

CROSS-REFERENCE TO RELATED U.S. PATENT APPLICATION

Cross-reference is made to U.S. Utility patent application Ser. No. 12/165,439 entitled "Tibial Bearing Having Increased Axial-Rotation" by Shouchen Dun, which was filed on Jun. 30, 2008, the entirety of which is incorporated herein by reference.

TECHNICAL FIELD

The present disclosure relates generally to orthopaedic prostheses, and particularly to posterior stabilized orthopaedic prostheses for use in knee replacement surgery.

BACKGROUND

Joint arthroplasty is a well-known surgical procedure by which a diseased and/or damaged natural joint is replaced by a prosthetic joint. A typical knee prosthesis includes a tibial tray, a femoral component, and a polymer insert or bearing positioned between the tibial tray and the femoral component. A knee prosthesis is generally designed to duplicate the natural movement of the patient's joint. However, depending on the severity of the damage to the patient's joint, orthopaedic prostheses of varying mobility may be used. For example, in some patients, the posterior cruciate ligament may be damaged, deficient, or removed during the orthopaedic surgical procedure. In such cases, a posterior stabilized knee orthopaedic prosthesis, which typically restricts or limits the posterior movement of the tibia relative to the femur, may be used.

SUMMARY

According to one aspect, an orthopaedic prosthesis may include a femoral component having a medial condyle and a lateral condyle. The medial condyle may include a lateral sidewall and the lateral condyle may include a medial sidewall. The lateral sidewall and the medial sidewall may define an intracondylar notch between the medial condyle and the lateral condyle. Additionally, the medial sidewall and the lateral sidewall may be tapered in the transverse plane. For example, the medial sidewall and the lateral sidewall taper toward each other in the transverse plane in the anterior-posterior direction.

In some embodiments, the femoral component may include a posterior cam and an anterior wall defined between the medial condyle and the lateral condyle. The anterior wall may be connected to the lateral sidewall of the medial condyle and the medial sidewall of the lateral condyle. The intracondylar notch may have a length when viewed in the transverse plane that is defined by a first line segment extending from a medial-lateral center point of a cam surface of the posterior cam to a medial-lateral center point of the anterior wall. Additionally, the intracondylar notch may have a first width defined by a second line segment orthogonal to and bisecting the first line segment, the second line segment extending from the medial sidewall to the lateral sidewall. Further, the intracondylar notch may have a second width defined by a third line segment orthogonal to the first line segment and crossing the first line segment at a point on the first line segment posterior to the second line segment. The third line segment may extend from the medial sidewall to the lateral sidewall. In some embodiments, the first width of the intracondylar notch may be greater than the second width of the intracondylar notch. For example, the intracondylar notch may have an anterior width and a posterior width. The anterior width may be greater than the posterior width in some embodiments. Additionally, in some embodiments, the femoral component may include a posterior cam. In such embodiments, the posterior cam may have a cam surface that is concave in the medial-lateral direction.

According to another aspect, a femoral component of an orthopaedic prosthesis may be configured to articulate with a tibial bearing of the orthopaedic prosthesis. The femoral component may include a pair of spaced-apart condyles. Each of the spaced-apart condyles may have a condylar surface. The femoral component may also include a cam box defined between the condylar surfaces of the spaced-apart condyles. The cam box may have an inner medial sidewall, an inner lateral sidewall, an inner anterior wall, and a posterior cam. The inner anterior wall may have a width defined between the inner medial sidewall and the inner lateral sidewall. Additionally, the posterior cam may have a width defined between the medial sidewall and the lateral sidewall. In some embodiments, the width of the inner anterior wall may be greater than the width of the posterior cam.

Additionally, in some embodiments, the inner medial sidewall and the inner lateral sidewall of the cam box are tapered in the transverse plane. For example, the inner medial sidewall and the inner lateral sidewall of the cam box may be tapered toward each other in the anterior-posterior direction. Additionally, in some embodiments, the posterior cam may include a cam surface that is concavely curved in the medial-lateral direction. The cam surface may also be convexly curved in the sagittal plane in some embodiments.

According to a further aspect, an orthopaedic prosthesis may include a tibial bearing configured to be coupled to a tibial tray and a femoral component configured to articulate with the tibial bearing. The tibial bearing may include a platform and a spine extending upwardly from the platform. The spine may include medial and lateral sidewalls. The femoral component may include a cam box defined by inner medial and lateral sidewalls. In some embodiments, the medial and lateral sidewalls of the spine may be tapered in the transverse plane. Additionally, in some embodiments, the inner medial and lateral sidewalls of the cam box may be tapered in the transverse plane. For example, in some embodiments, the medial and lateral sidewalls of the spine may be tapered in the anterior-posterior direction and the medial and lateral sidewalls of the cam box may be tapered in the anterior-posterior direction.

In some embodiments, the platform may have a centerline axis defined in the anterior-posterior direction when viewed in the transverse plane. Additionally, in some embodiments, the spine may have a longitudinal axis that is angled with respect to the centerline axis of the platform. The cam box may include an inner anterior wall and a posterior cam in some embodiments. The inner anterior wall may have a width defined between the inner medial sidewall and the inner lateral sidewall. The posterior cam may have a width defined between the inner medial sidewall and the inner lateral sidewall. In some embodiments, the width of the inner anterior wall may be greater than the width of the posterior cam.

Additionally, in some embodiments, the platform may include an anterior rim and the spine may have a length when viewed in the transverse plane that is defined by a first line segment extending from a medial-lateral center point of a posterior cam surface of the spine to a medial-lateral center point of the anterior rim of the platform. The spine may also have a first width defined by a second line segment orthogonal to and bisecting the first line segment. The second line segment may extend from the medial sidewall to the lateral sidewall of the spine. Additionally, the spine may have a second width defined by a third line segment orthogonal to the first line segment and crossing the first line segment at a point on the first line segment posterior to the second line segment. The third line segment may extend from the medial sidewall to the lateral sidewall of the spine. In some embodiments, the first width of the spine may be greater than the second width of the spine. Further, in some embodiments, the width of the anterior wall of the cam box of the femoral component may be greater than the first width of the spine.

In some embodiments, the spine of the tibial bearing may include a posterior cam surface. In such embodiments, the posterior cam surface may be convexly curved in the transverse plane. Additionally, in such embodiments, the posterior cam of the femoral component may include a cam surface configured to initially contact the posterior cam surface of the tibial bearing at a first degree of flexion. The cam surface of the posterior cam may be concavely curved in the medial-lateral direction. Additionally, the femoral component may be configured to rotate about an axis defined by the spine of the tibia bearing during a range of degrees of flexion greater than the first degree of flexion.

In some embodiments, the inner medial sidewall of the cam box may contact the medial sidewall of the spine at a first degree of flexion. Additionally or alternatively, the inner lateral sidewall of the cam box may contact the lateral sidewall of the spine at the first degree of flexion. In some embodiments, the first degree of flexion may be about 30 degrees.

BRIEF DESCRIPTION OF THE DRAWINGS

The detailed description particularly refers to the accompanying figures in which:

FIG. 5 is a cross-sectional view of the tibial bearing of FIG. 2 taken generally along the line 5-5;

FIG. 6 is another cross-sectional view of the tibial bearing of FIG. 2 taken generally along the line 6-6;

DETAILED DESCRIPTION OF THE DRAWINGS

Figure 1:
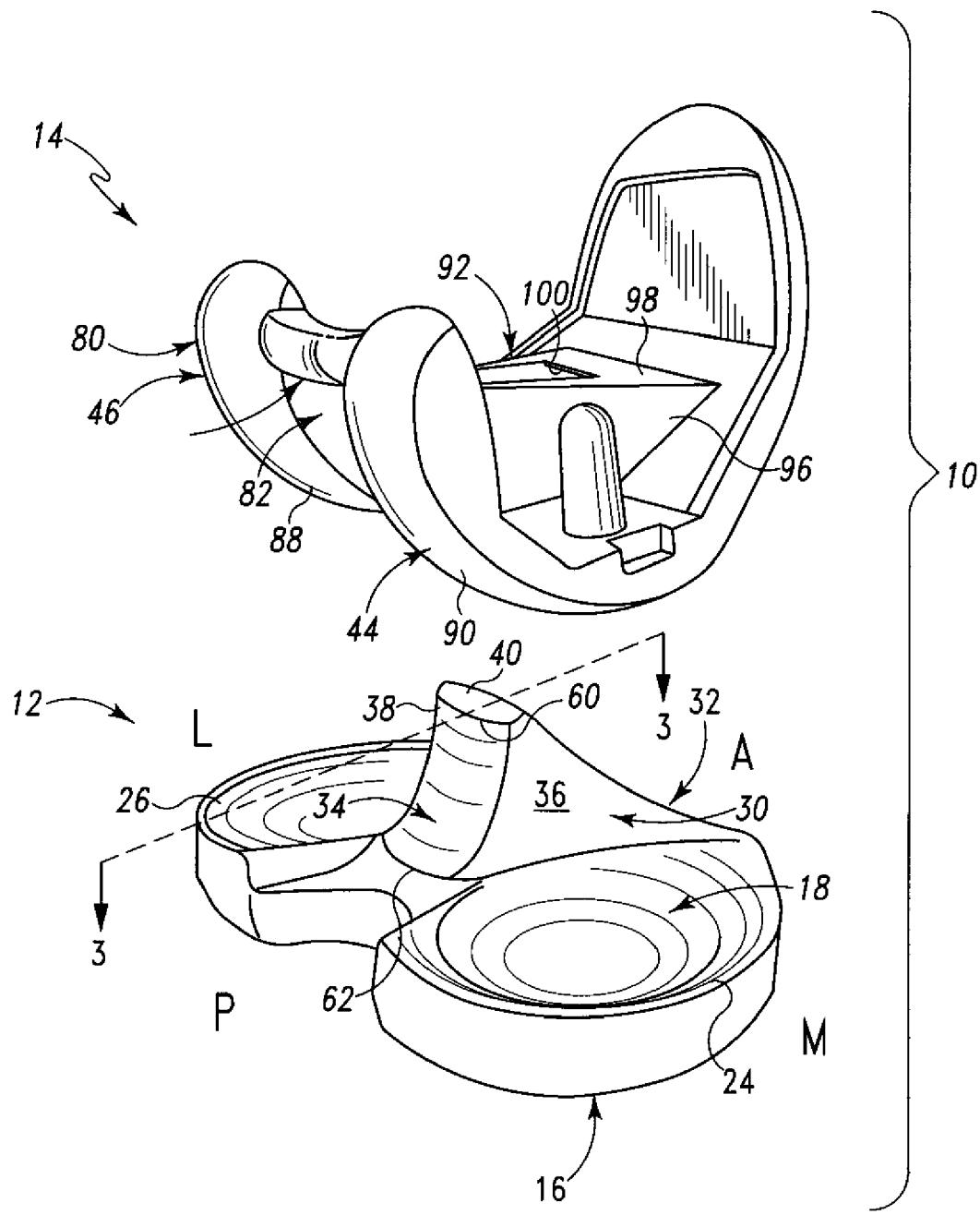
FIG. 1 is a perspective view of one embodiment of an orthopaedic knee prosthesis.

While the concepts of the present disclosure are susceptible to various modifications and alternative forms, specific exemplary embodiments thereof have been shown by way of example in the drawings and will herein be described in detail. It should be understood, however, that there is no intent to limit the disclosure to the particular forms disclosed, but on the contrary, the intention is to cover all modifications, equivalents, and alternatives following within the spirit and scope of the invention as defined by the appended claims.

Terms representing anatomical references, such as anterior, posterior, medial, lateral, superior, inferior, etcetera, may be used throughout this disclosure in reference to both the orthopaedic implants described herein and a patient's natural anatomy. Such terms have well-understood meanings in both the study of anatomy and the field of orthopaedics. Use of such anatomical reference terms in the specification and claims is intended to be consistent with their well-understood meanings unless noted otherwise.

Referring now to FIG. 1, in one embodiment, a posterior stabilized orthopaedic knee prosthesis 10 includes a tibial insert or bearing 12, a femoral component 14, and, in some embodiments, a tibial tray (not shown). The femoral component 14 is configured to articulate with the tibial bearing 12 during use. In particular, the knee prosthesis 10 is configured to promote external axial rotation of the femoral component 14 with respect to the tibial bearing 12 during flexion of a patient's knee as discussed in more detail below.

It should be appreciated that the orthopaedic knee prosthesis 10 is illustrated as and discussed below in regard to a left knee prosthesis, which is configured to replace the left knee of a patient. However, in other embodiments, the orthopaedic knee prosthesis 10 may be embodied as a right knee prosthesis configured to replace a right knee of a patient. Regardless, it should be appreciated that the concepts and features discussed and illustrated herein are applicable to both left and right knee orthopaedic prostheses.

The tibial bearing 12 is illustratively formed from a polymer material such as ultra-high molecular weight polyethylene (UHMWPE), but may be formed from other materials, such as a ceramic material, a metallic material, a bio-engineered material, or the like, in other embodiments. Additionally, in the illustrative embodiment, the tibial bearing 12 is embodied as a fixed tibial bearing which may be limited or restricted from rotating relative to the tibial tray.

As shown in FIG. 1, the tibial bearing 12 includes a platform 16 having an upper bearing surface 18 and a bottom surface 20. Illustratively, the bearing 12 may also include other devices or features to secure the tibial bearing 12 to the tibial tray in a non-rotating configuration. The upper bearing surface 18 of the tibial bearing 12 includes a medial bearing surface 24 and a lateral bearing surface 26. The medial and lateral bearing surfaces 24, 26 are configured to receive or otherwise contact corresponding medial and lateral condyles 44, 46 of the femoral component 14, as is discussed in greater detail below. As such, the bearing surfaces 24, 26 may have concave contours in some embodiments.

Figure 2:
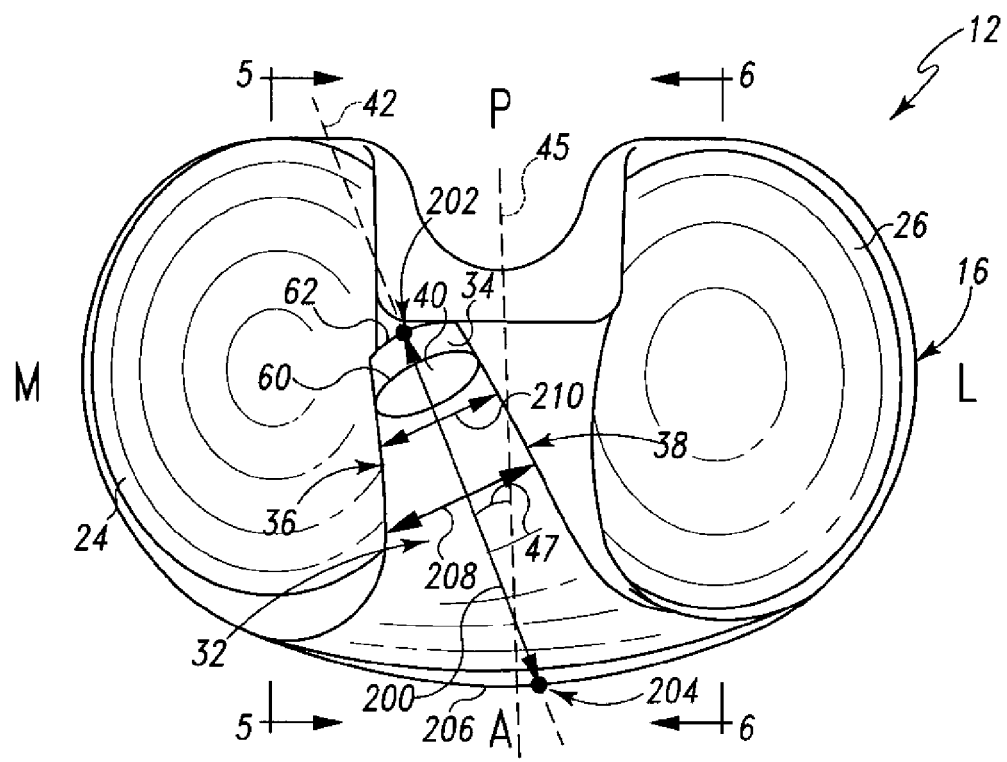
FIG. 2 is a plan view of a tibial bearing of the orthopaedic knee prosthesis of FIG. 1.

A spine 30 of the bearing 12 extends upwardly from the platform 16 and is positioned between the bearing surfaces 24, 26. The spine 30 includes an anterior surface 32, a posterior cam surface 34, a medial sidewall 36, and a lateral sidewall 38. The spine 30 further includes a superior surface 40. Illustratively, as shown in FIG. 2, the spine 30 is angled toward the medial bearing surface 24 of the platform 16 as the spine 30 extends posteriorly. In other words, the spine 30 is angled medially from the anterior surface 32 to the posterior cam surface 34 of the spine 30 in the transverse plane. As such, a longitudinal axis 42 of the spine 30, when viewed in the transverse plane is angled with respect to a centerline axis 45 of the platform 16 extending in the anterior-posterior direction. The longitudinal axis 42 and the centerline axis 45 define an angle 47 therebetween. In some embodiments, spine 30 is configured such that the angle 47 is greater than about five degrees. For example, in one particular embodiment, the angle 47 is about eight degrees. Additionally, in another particular embodiment, the angle 47 is from about ten degrees to about fifteen degrees. However, it is within the scope of this disclosure for the angle between the centerline axes 42, 45 to be any suitable angle. As is discussed in greater detail below, the angle 47 of the spine 30 facilitates outward axial rotation of the femoral component 14 relative to the tibial bearing 12. In particular, the amount of axial rotation of the femoral component 14 is related to the degree or angle 47 of the spine 30. In other words, an increased amount of rotation during flexion of the orthopaedic prosthesis may be obtained by increasing the angle 47 whereas a decreased amount of rotation during flexion may be obtained by decreasing the angle 47.

Referring again to FIG. 2, the spine 30 of the tibial bearing 12 is also tapered in the anterior-posterior direction in the transverse plane. In other words, the medial and lateral surfaces, or sidewalls, 36, 38 of the spine 30 converge toward each other from the anterior surface 32 of the spine 30 to the posterior surface 34 of the spine 30. For example, in some embodiments, the surface 36, 38 may define a respective planes, which taper toward each other and are configured to intersect each other at some location posterior to the spine 30.

As such, the spine 30 may have a substantially decreasing width in the anterior-posterior direction. That is, the spine 30 may have an anterior width that is greater than a posterior width. For example, in one embodiment, the spine 30 may have a length when viewed in the transverse plane defined by a line segment 200 extending from a center point 202 of the posterior cam surface 34 to a center point 204 of an anterior rim 206 of the platform 16. The spine 30 also has an illustrative anterior width defined by a line segment 208 extending from the lateral sidewall 38 to the medial sidewall 36. The line segment 208 is orthogonal to and bisects the line segment 200. The spine 30 also has an illustrative posterior width (with respect as to the anterior width) defined by a line segment 210 extending from the lateral sidewall 38 to the medial sidewall 36. The line segment 210 is orthogonal to the line segment 200 and is positioned posteriorly with respect to the line segment 208. In some embodiments, the anterior width of the spine 30 is greater than the posterior width of the spine 30. That is, the length of the line segment 208 is greater than the length of the line segment 210. For example, in some embodiments, the line segment 208 may have a length that is greater than the length of the line segment 210 by at least 0.1 millimeters. As such, in some embodiments, the spine 30 may be angled and tapered in the anterior-to-posterior direction.

Figure 3:
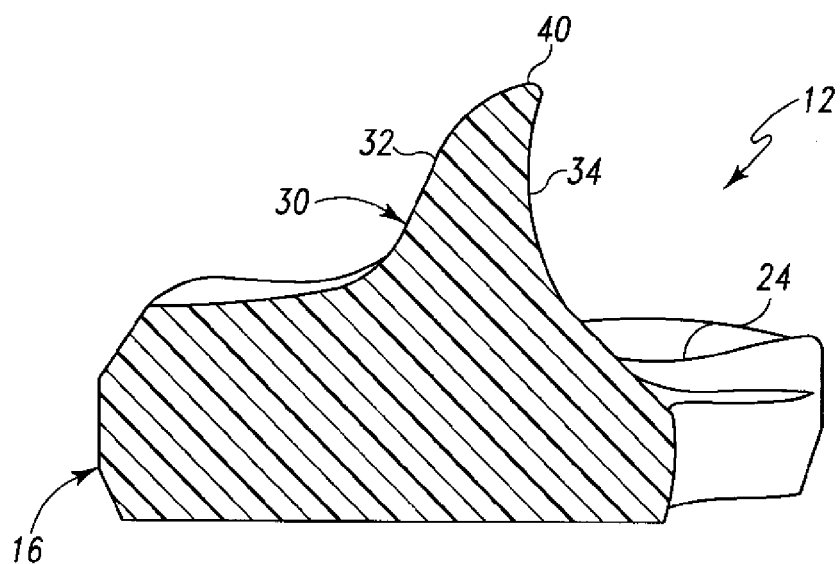
FIG. 3 is a cross-sectional view of the tibial bearing of FIG. 2 taken generally along the line 3-3 of FIG. 1.
Figure 4:
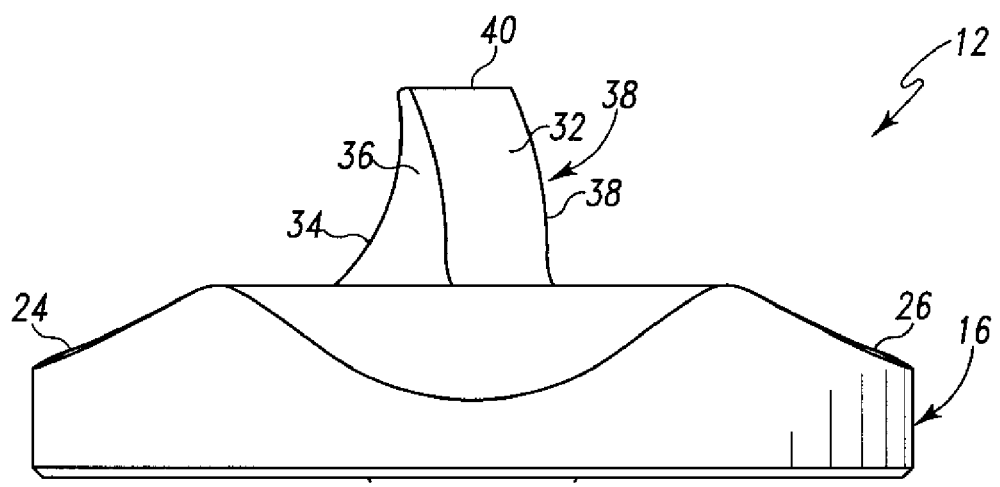
FIG. 4 is an anterior elevational view of the tibial bearing of FIG. 2.

Referring now to FIGS. 2-4, the posterior cam surface 34 of the spine 30 is concave in the sagital plane (see FIG. 3) and is convex in the transverse plane (see FIG. 2). In other words, as shown in FIG. 2, the posterior cam surface 34 of the spine 30 bows outwardly posteriorly to define a convex superior edge 60 of the posterior surface 34 of the spine 30 and a convex inferior edge 62 of the posterior surface 34 of the spine 30. As is discussed in greater detail below, this posterior bowing of the posterior surface 34 of the spine 30 in the transverse plane also facilitates axial rotation of the femoral component 14 relative to the tibial bearing 12 during flexion as the spine 30 of the tibial bearing 12 interacts with a posterior cam 64 of the femoral component 14. Further illustratively, the outwardly curved posterior surface 34 of the spine 30 may operate to prevent edge loading during axial rotation of the femoral component 14 relative to the tibial bearing 12.

Referring now to FIGS. 5 and 6, the medial condylar bearing surface 24 and the lateral condylar bearing surface 26 of the platform 16 are concavely curved in the sagittal plane. In some embodiments, the lateral condylar bearing surface 26 is less constrained in the posterior region of the surface 26 with respect to the medial condylar bearing surface 24. For example, as shown in FIG. 5, the medial bearing surface 24 in the sagittal plane may be defined by a first radius of curvature 70. Additionally, in some embodiments, the posterior half of the medial bearing surface 24 in the sagittal plane may be defined by a second radius of curvature 72. However, it should be appreciated that while two radii of curvature 70, 72 are disclosed, it is within the scope of this disclosure to provide a lateral medial surface 24 defined by a single radius of curvature or by any suitable number of radii of curvature. Illustratively, the second radius of curvature 72 is smaller than the first radius of curvature 70. However, it is within the scope of this disclosure for the anterior and posterior portions of the medial bearing surface to have any suitable radii of curvature.

Further illustratively, as shown in FIG. 6, the lateral bearing surface 26 is defined by a third radius of curvature 74 in the sagital plane. Illustratively, the posterior and anterior half of the lateral bearing surface 26 in the sagittal plane are defined by the same radius of curvature 74. However, it is within the scope of this disclosure to include a tibial bearing having a lateral bearing surface which defines multiple radii of curvature. Illustratively, the second, posterior radius of curvature 72 of the posterior half of the medial bearing surface 24 is smaller than the third, posterior radius of curvature of the posterior half of the lateral bearing surface 26. The third radius of curvature 74 may be greater than, less than, or generally equal to the first radius of curvature 70 of the medial bearing surface 24. For example, in one embodiment, the radius of curvature 74 is greater than the radius of curvature 70 by at least 0.5 millimeters. However, it is within the scope of this disclosure for the posterior half of the lateral bearing surface 26 to have any suitable radius of curvature greater than the radius of curvature of the posterior half of the medial bearing surface 24. Accordingly, the posterior region of the medial bearing surface 24 is more constrained than a posterior region of the lateral bearing surface 26. As such, the less constrained posterior region of the lateral bearing surface 26 facilitates outward axial rotation of the femoral component 14 in deep or late flexion, as is discussed in greater detail below.

Figure 7:
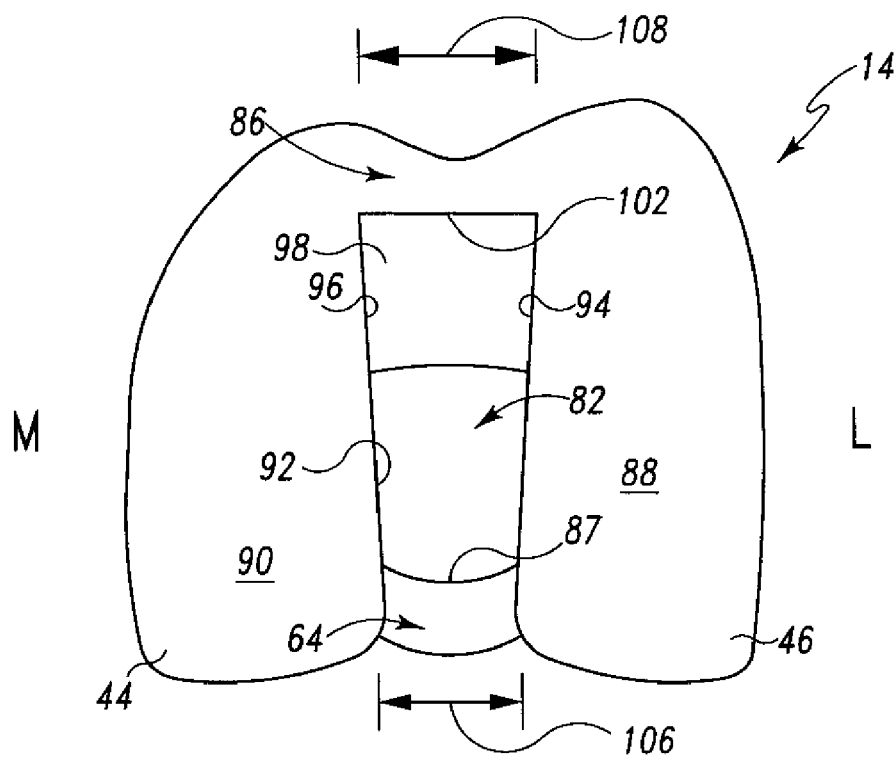
FIG. 7 is an inferior elevational view of a femoral component of the orthopaedic knee prosthesis of FIG. 1.
Figure 8:
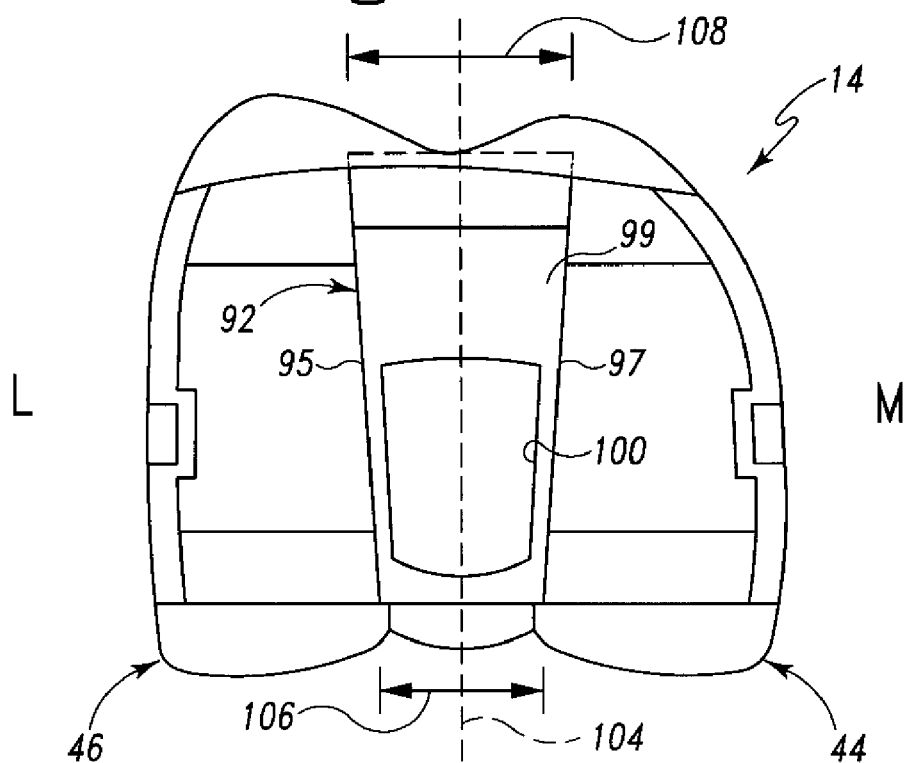
FIG. 8 is a superior elevational view of the femoral component of FIG. 7.

Looking now to FIGS. 7 and 8, the femoral component 14 is configured to be coupled to a surgically-prepared surface of the distal end of a patient's femur (not shown). The femoral component 14 may be secured to the patient's femur via use of bone adhesive or other attachment means. The femoral component 12 is illustratively formed from a metallic material such as cobalt-chromium or titanium, but may be formed from other materials, such as a ceramic material, a polymer material, a bio-engineered material, or the like, in other embodiments.

The femoral component 14 includes an articulating surface 80 having a pair of spaced-apart medial and lateral condyles 44, 46 having respective medial and lateral condyle surfaces 88, 90. In use, the condyles 44, 46 replace the natural condyles of the patient-3 s femur and are configured to articulate on the corresponding bearing surfaces 24, 26 of the platform 16 of the tibial bearing 12.

The condyles 44, 46 are spaced-apart to define an intracondyle notch or recess 82 therebetween. The posterior cam 64 is positioned in the intracondyle notch 82. The posterior cam 64 is located toward the posterior side of the femoral component 14 and includes a cam surface 87 configured to engage or otherwise contact the posterior cam surface 34 of spine 30 of the tibial bearing 12 during flexion as described in more detail below.

Illustratively, the posterior cam surface 87 of the femoral component is concavely curved in the medial-lateral direction as illustrated in FIG. 7. The posterior cam surface 34 of the spine 30 is convex in the traverse plane as illustrated in FIG. 4. Illustratively, the radius of curvature of the cam surfaces 87, 34 may be dependent upon a number of criteria such as the size of the prosthesis, the shape or geometry of the articulating surface of the spine 30 of the tibial implant 12, the shape or geometry of the articulating surface of the cam 64, and/or the like.

The intracondylar notch 82 is defined by a cam box 92. The cam box 92 includes an inner medial wall 96, which is connected to a lateral edge of the medial condyle 90, and an inner lateral wall 94, which is connected to a medial edge of the lateral condyle 88. The cam box 92 also includes an anterior wall 86, which may be embodied as an anterior cam in some embodiments. In such embodiments, the anterior cam includes an anterior cam surface 102. The cam box 92 also includes the posterior cam 64, which forms an inner posterior "wall" of the cam box 92.

The cam box 92 also includes a superior wall 98. Illustratively, the superior wall 98 includes an aperture 100 formed therethrough. The aperture 100 is configured to receive a femoral stem (not shown) to be received with in a bore drilled into the femur of a patient. Additionally, as shown in FIG. 7, the cam box 92 includes an outer medial sidewall 97 and an outer lateral sidewall 95

In embodiments wherein the anterior wall 86 is embodied as an anterior cam, the cam surface 102 may be generally straight in the medial-lateral direction, as shown in FIG. 7. However, it is within the scope of this disclosure to include a curved cam surface as well. Illustratively, the cam surface 102 of the anterior cam 86 may interact with the anterior surface 32 of the spine 30 of the tibial bearing 12 during extension. Further illustratively, although the femoral component includes the cam box 92 having the convex anterior cam 86, it is within the scope of this disclosure to include an anterior cam having another suitable cam surface to interact with the corresponding anterior surface of the spine of the tibial bearing. Further, it is within the scope of this disclosure to provide a cam box without an anterior cam. In other words, it is within the scope of this disclosure to provide a cam box having only a posterior cam, such as the posterior cam 64.

Referring again to FIGS. 7 and 8, the inner medial and lateral sidewalls 96, 94 of the cam box 92 are tapered in the transverse plane. In particular, the sidewalls 94, 96 taper toward each other from the anterior side of the femoral component 14 to the posterior side of the femoral component 14. Accordingly, the medial sidewall 96 is angled with respect to a longitudinal axis 104 of the cam box 92 of the femoral component 14. The lateral sidewall 94 is similarly angled with respect to the longitudinal axis 104 of the cam box 92 of the femoral component 14.

Illustratively, the cam box 92 has a posterior width 106 and an anterior width 108. The posterior width 106 may be equal to a width of the posterior cam 64 between the medial sidewall 96 and the lateral sidewall 94. Similarly, the anterior width 108 may be equal to a width of the anterior wall 86 between the medial sidewall 96 and the lateral sidewall 94. As shown in FIGS. 7 and 8, the anterior width 108 is greater than the posterior width 106. For example, in some embodiments, the anterior width 108 may be greater than the posterior width 106 by 0.5 millimeters or more. However, it is within the scope of this disclosure to include a cam box having any suitable posterior width that is less than the anterior width of the cam box. It is also noted that similar to the spine 30, the distance between the medial and lateral sidewalls 96, 94 of the cam box 92, which is perpendicular to the longitudinal axis 104 of the cam box 92, decreases in a posterior direction.

Illustratively, a medial-lateral width of the cam box 92 between the sidewalls 94, 96 is greater than a medial-lateral width of the spine 30 along similar anterior-posterior positions. In particular, any width of the cam box 92 taken generally in the anterior half of the cam box 92 is wider than the widest portion, i.e., the anterior width 208, of the spine 30. Therefore, the spine 30 generally does not contact the sidewalls 94, 96 of the cam box 92 in early flexion in order to allow the femoral component 14 to remain in a neutral axial position, i.e., having no rotation of the femoral component 14 on the tibial component 12, during early flexion. For example, in some embodiments, the femoral component 14 may remain in a neutral axial position during the first 30 degrees of knee flexion. However, it is within the scope of this disclosure to include a knee prosthesis wherein the femoral component remains in a neutral axial position during any suitable portion of the knee flexion. In other words, it is within the scope of this disclosure to include a knee prosthesis which facilitates the outward axial rotation of the femoral component at some time before or after 30 degrees of knee flexion.

As stated above, the femoral component 14 articulates on the tibial bearing 12 and is urged to rotate outwardly axially in later flexion. Illustratively, as noted above, the angled and tapered spine 30 of the tibial bearing 12 as well as the tapered cam box 92 of the femoral component cooperate to promote outward axial rotation of the femoral component 14 on the tibial bearing 12. Further, the less constrained posterior portion of the lateral bearing surface 26 also promotes such outward axial rotation of the femoral component during flexion. Additionally, the cam surface 34 of the spine 30 is curved posteriorly in the transverse plane and the posterior cam 64 of the femoral component 12 articulates on the cam surfaces 34 in the transverse plane such that rotation of the femoral component 14 about the spine 30 is further facilitated.

Figure 10:
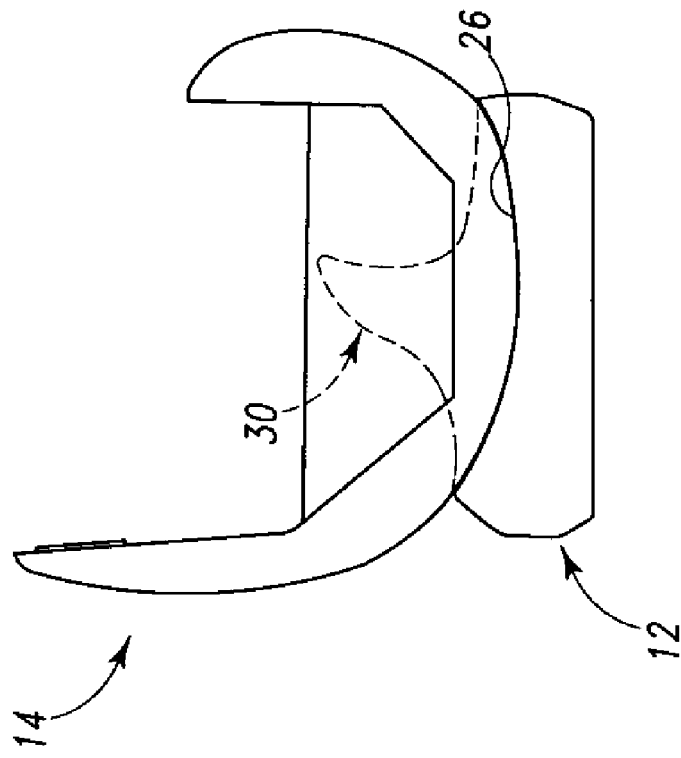
FIG. 10 is a side elevational view of the assembled orthopaedic knee prosthesis of FIG. 9.
Figure 9:
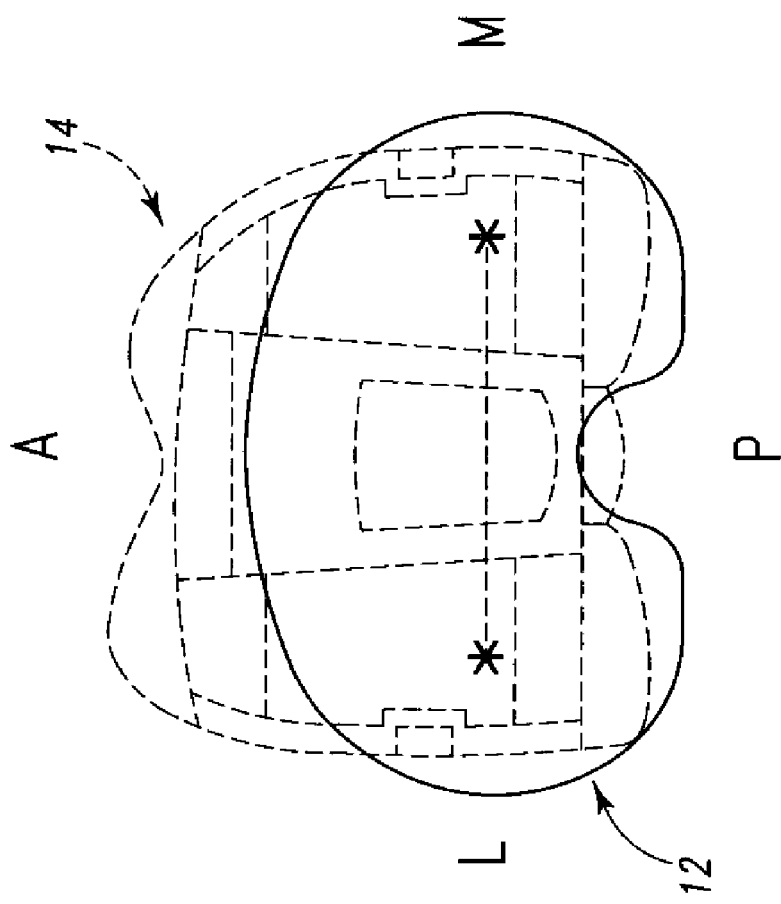
FIG. 9 is a schematic diagram of a superior plan view of the femoral component and tibial bearing of the orthopaedic knee prosthesis of FIG. 1 in an assembled configuration and positioned at about 0 degrees of flexion.
Figure 12:
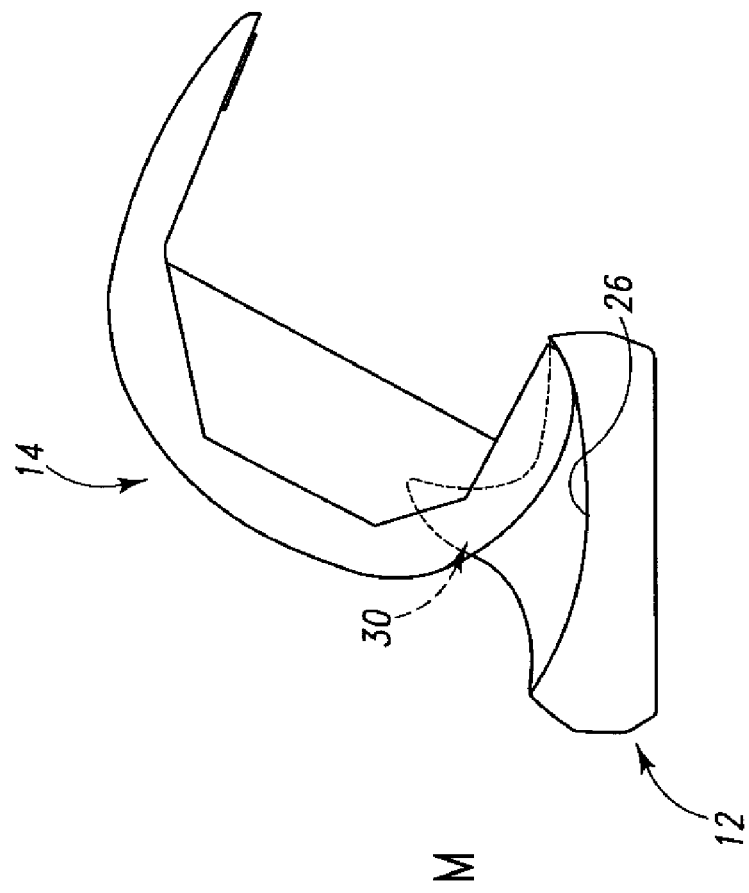
FIG. 12 is a side elevational view of the assembled orthopaedic knee prosthesis of FIG. 11.
Figure 11:
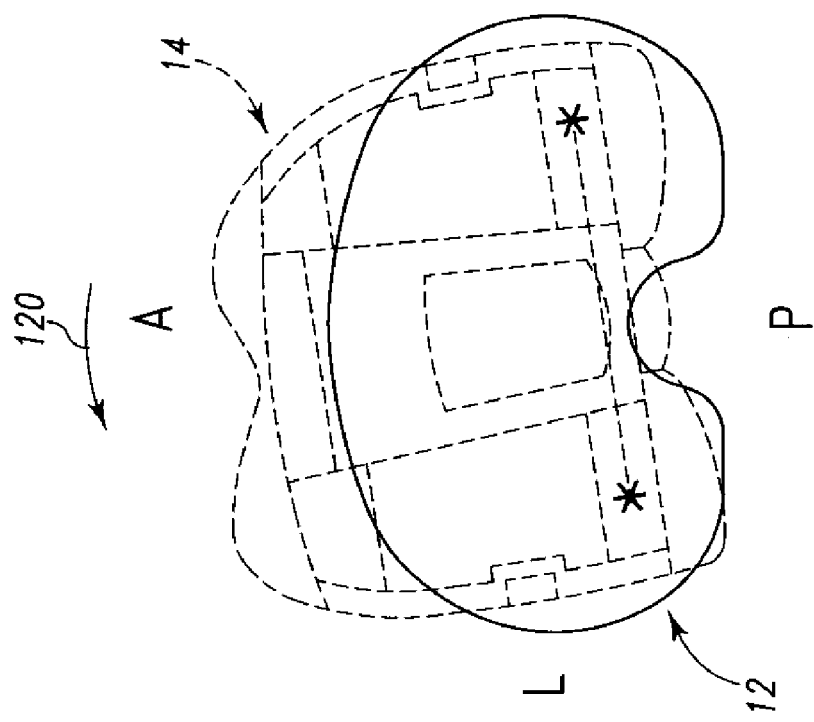
FIG. 11 is a schematic diagram of a superior plan view of the assembled orthopaedic knee prosthesis of FIG. 9 positioned in deep flexion.

For example, the angled and tapered spine 30 of the tibial bearing 12 cooperates with the tapered cam box 92 during flexion to facilitate axial rotation of the femoral component 14 on the tibial component 12, as shown in FIGS. 11 and 12. Illustratively, the spine 30 is positioned within the intracondyle notch 82, which is substantially defined by the cam box 92, of the femoral component 14. Illustratively, as noted above, the cam box 92 is sufficiently wide to allow the femoral component 14 to stay in a neutral axial position, i.e., having 0 degrees of rotation, relative to the tibial bearing 12, during early knee flexion. For example, as shown in FIGS. 9 and 10, the femoral component 14 is in an axial neutral position at 0 degrees of flexion. This axially neutral position is maintained throughout approximately the first 30 degrees of flexion, as noted above. In other words, the cam box 92 is wide enough to prevent the spine 30 from engaging the sidewalls 94, 96 of the cam box 92 during early flexion.

At approximately 30 degrees of flexion, the sidewalls 94, 96 of the cam box 92 begin to engage with the sidewalls 36, 38 of the spine 30. As such, the angled spine 30 interacts with the cam box 92 to guide the femoral component 14 and axially rotate the femoral component 14 outwardly on the tibial bearing 12. Further illustratively, the tapered sidewalls 36, 38 of the spine 30 and the tapered sidewalls 94, 96 of the cam box 92 cooperate with each other to suitably accommodate the angled spine 30.

Accordingly, the angled spine 30 facilitates rotation of the femoral component 14 outwardly, or in a generally counter-clockwise direction 120, as shown in FIG. 11, during later flexion of the knee. As the knee continues to flex, the sidewalls 94, 96 of the cam box 92 and the sidewalls 36, 38 of the spine 30 continue to engage each other resulting in a gradually increased axial rotation of the femoral component 14. As noted below, this process is facilitated by the less-constrained posterior portion of the lateral bearing surface 26 of the tibial bearing 12. The amount of rotation between the femoral component 14 and the tibial bearing 12 during flexion may be adjusted based on the degree of the angle 47 of the spine 30 between the centerline axis of the tibial bearing 45 and the centerline axis of the spine 42. For example, an increased amount of rotation of the femoral component 14 on the tibial bearing 12 may be obtained by increasing the angle 47 of the spine 30.

As noted above, the radii of curvature of the medial and lateral bearing surfaces 24, 26 of the tibial bearing 12 further cooperate with the femoral component 14 to promote the outward axial rotation of the femoral component 14 on the tibial component 12 during flexion. For example, the posterior portion of the lateral bearing surface 26 is less constrained than the posterior portion of the medial bearing surface 24. As discussed above, the posterior radius of curvature 74 of the lateral bearing surface 26 is greater than the posterior radius of curvature 72 of the medial bearing surface 26, thus providing a less constrained posterior bearing surface 26. During later flexion, therefore, the lateral condyle 46 of the femoral component 14 is less constrained within the lateral bearing surface 26 of the tibial bearing 12 when the lateral condyle 46 is engaged with the posterior portion of the lateral bearing surface 26. Accordingly, therefore, the lateral condyle 46 of the femoral component 14 is able to move posteriorly on the lateral bearing surface 26, as shown in deep flexion in FIGS. 11 and 12, to promote the outward axial rotation of the femoral component 14.

As further noted above, the femoral component 14 and the tibial bearing 12 are configured such that the posterior cam 64 of the femoral component 14 contacts the spine 30 of the tibial bearing 12 during flexion. In particular, during flexion, the concave cam surface 87 of the posterior cam 64 of the femoral component 14 contacts the convex cam surface 34 of the spine 30. Accordingly, the interaction between the cam surfaces 34, 87 allows the femoral component 14 to rotate axially relative to the tibial bearing 12 during flexion. In some embodiments, the radius of curvature in the medial-lateral direction of the concave cam surface 87 may be substantially equal to, greater than, or less than the radius of curvature in the transverse plane of the convex cam surface 34 of the spine 30. Illustratively, the concave cam surface 87 of the posterior cam 64 operates to increase the contact area between the posterior surface 34 of the spine 30 and the cam 64. This increase in contact area may decrease the stress between the cam surfaces 34, 87 during axial rotation of the femoral component 14 relative to the tibial bearing 12. Further, the amount of rotation between the femoral component 14 and the tibial bearing 14 during flexion may be adjusted based on the radius of curvatures in the transverse plane of the cam surfaces 34, 87. For example, an increased amount of rotation during flexion of the orthopaedic prosthesis may be obtained by decreasing the radius of curvature in the transverse plane of the convex cam surface 87. Illustratively, while the cam surface 87 of the posterior cam 64 is curved posteriorly, the cam surface 87 may also be substantially planar in the medial-lateral direction in some embodiments.

Illustratively, when the orthopaedic prosthesis 10 is extended or otherwise not in flexion (e.g., a neutral position of about 0 degrees flexion), the posterior cam 64 of the femoral component 14 is not in contact with the spine 30 of the tibial bearing 12. However, late flexion the posterior cam 64 of the femoral component 14 contacts the spine 30 of the tibial bearing 12. Illustratively, for example, in some embodiments, the posterior cam 64 may engage the spine 30 at approximately 70 degrees of flexion. As noted above, during late or deep flexion of the orthopaedic prosthesis 10, the convex cam surface 34 of the spine 30 maintains contact with the concave cam surface 87 of the femoral component 14. It should be appreciated that contact between the posterior cam 64 and the spine 30 is maintained during late flexion.

For example, contact between the concave cam surface 87 of the posterior cam 64 of the femoral component 14 and the convex cam surface 34 of the spine 30 during late flexion may facilitate rollback of the femoral component 14 on the platform 16 of the tibial bearing 12. Furthermore, as noted above, during flexion, the femoral component 14 may rotate about the spine 30 in the generally counter-clockwise or outward axial direction in the transverse plane as indicated by arrow 120 in FIG. 11. The amount of rotation between the femoral component 14 and the tibial bearing 12 during flexion may be adjusted based on the radius of curvatures in the transverse plane of the cam surfaces 34, 87. However, as noted above, the amount of axial rotation of the femoral component 14 relative to the tibial bearing 12 is substantially dependent upon the spine angle 47 and the interaction between the sidewalls 36, 38 of the spine 30 and the sidewalls 94, 96 of the cam box 92.

Illustratively, many features of the prosthesis 10 cooperate to facilitate outward axial rotation of the femoral component 14 on the tibial bearing 12. While these features are shown and described on a common prosthesis 10, it is within the scope of this disclosure to include a knee prosthesis having only one or more of the above-disclosed features which promote the outward axial rotation of the femoral component 14 and which cooperate with and accommodate such features.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the concepts of the present disclosure arising from the various features of the systems described herein. It will be noted that alternative embodiments of each of the systems of the present disclosure may not include all of the features described yet still benefit from at least some of the advantages of such features. Those of ordinary skill in the art may readily devise their own implementations of a system that incorporate one or more of the features of the present disclosure and fall within the spirit and scope of the invention as defined by the appended claims.

The invention claimed is:

1. An orthopaedic knee prosthesis comprising:
   a tibial bearing configured to be coupled to a tibial tray, the tibial bearing having a platform including a medial condylar bearing surface and a lateral condylar bearing surface and a spine extending upwardly from the platform and positioned between said medial and lateral bearing surfaces, the spine including an anterior surface, a posterior cam surface, a medial sidewall, and a lateral sidewall; and
   a femoral component configured to articulate with the tibial bearing, the femoral component having a pair of spaced-apart medial and lateral condyles and a cam box therebetween, the cam box defined by an inner anterior wall, a posterior cam, an inner medial sidewall, and an inner lateral sidewall, wherein (i) the medial and lateral sidewalls of the spine are tapered in the anterior-posterior direction when viewed in the transverse plane and (ii) the inner medial and lateral sidewalls of the cam box are tapered in the anterior-posterior direction when viewed in the transverse plane, wherein the posterior cam surface of the spine is convex in the transverse plane, and is concave in the sagittal plane, and wherein the platform has a centerline axis defined in the anterior-posterior direction when viewed in the transverse plane, and the spine has a longitudinal axis that is angled with respect to the centerline axis of the platform when viewed in the transverse plane.

2. The orthopaedic knee prosthesis of claims 1, wherein: the inner anterior wall has a width defined between the inner medial sidewall and the inner lateral sidewall, (ii) the posterior cam has a width defined between the inner medial sidewall and the inner lateral sidewall, and (iii) the width of the inner anterior wall is greater than the width of the posterior cam.

3. The orthopaedic knee prosthesis of claim 2, wherein the posterior cam of the femoral component includes a cam surface that is concave in the medial-lateral direction.

4. The orthopaedic knee prosthesis of claim 3, wherein the cam surface is convex in the sagittal plane.

5. The orthopaedic knee prosthesis of claim 2, wherein (i) the platform includes an anterior rim, (ii) the spine has a length when viewed in the transverse plane that is defined by a first line segment extending from a medial-lateral center point of the posterior cam surface of the spine to a medial-lateral center point of the anterior rim of the platform,
  (iii) the spine has a first width defined by a second line segment orthogonal to and bisecting the first line segment, the second line segment extending from the medial sidewall to the lateral sidewall of the spine,
  (iv) the spine has a second width defined by a third line segment orthogonal to the first line segment and crossing the first line segment at a point on the first line segment posterior to the second line segment, the third line segment extending from the medial sidewall to the lateral sidewall of the spine, and
  (v) the first width of the spine being greater than the second width of the spine.

6. The orthopaedic knee prosthesis of claim 5, wherein the width of the inner anterior wall of the cam box of the femoral component is greater than the first width of the spine.

7. The orthopaedic knee prosthesis of claim 1, wherein: the posterior cam of the cam box includes a cam surface configured to initially contact the posterior cam surface of the tibial bearing at a first degree of flexion, the cam surface of the posterior cam being concavely curved in the medial-lateral direction.

8. The orthopaedic knee prosthesis of claim 7, wherein the femoral component is configured to rotate about an axis defined by the spine of the tibial bearing during a range of degrees of flexion greater than the first degree of flexion.

9. The orthopaedic knee prosthesis of claim 1, wherein the inner medial sidewall of the cam box contacts the medial sidewall of the spine at a first degree of flexion and the inner lateral sidewall of the cam box contacts the lateral sidewall of the spine at the first degree of flexion.

10. The orthopaedic knee prosthesis of claim 9, wherein the first degree of flexion is about 30 degrees.

11. The orthopaedic knee prosthesis of claim 1, wherein the inner lateral sidewall and the inner medial sidewall define an intracondylar notch between the medial condyle and the lateral condyle.

12. The orthopaedic knee prosthesis of claim 11, wherein:
  (i) the inner anterior wall of the cam box is connected to the inner lateral sidewall of the medial condyle and the inner medial sidewall of the lateral condyle,
  (ii) the intracondylar notch has a length when viewed in the transverse plane that is defined by a first line segment extending from a medial-lateral center point of a cam surface of the posterior cam to a medial-lateral center point of the inner anterior wall,
  (iii) the intracondylar notch has a first width defined by a second line segment orthogonal to and bisecting the first line segment, the second line segment extending from the inner medial sidewall to the inner lateral sidewall,
  (iv) the intracondylar notch has a second width defined by a third line segment orthogonal to the first line segment and crossing the first line segment at a point on the first line segment posterior to the second line segment, the third line segment extending from the inner medial sidewall to the inner lateral sidewall, and
  (v) the first width of the intracondylar notch being greater than the second width of the intracondylar notch.

13. The orthopaedic knee prosthesis of claim 11, wherein the posterior cam has a cam surface that is concave in the medial-lateral direction.

* * * * *